(12) United States Patent
Kimura

(10) Patent No.: US 9,297,980 B2
(45) Date of Patent: Mar. 29, 2016

(54) OPTICAL DEVICE FOR TRANSMISSION-TYPE SCANNING BY MOVING SCANNING BEAM WITHOUT MOVING OBSERVATION SAMPLE

(71) Applicant: HITACHI-LG DATA STORAGE, INC., Minato-ku, Tokyo (JP)

(72) Inventor: Shigeharu Kimura, Yokohama (JP)

(73) Assignee: HITACHI-LG DATA STORAGE, INC., Tokyo (JP)

( * ) Notice: Subject to any disclaimer, the term of this patent is extended or adjusted under 35 U.S.C. 154(b) by 107 days.

(21) Appl. No.: 13/965,514

(22) Filed: Aug. 13, 2013

(65) Prior Publication Data
US 2014/0063495 A1  Mar. 6, 2014

(30) Foreign Application Priority Data
Aug. 29, 2012  (JP) .................................. 2012-188375

(51) Int. Cl.
| | | |
|---|---|---|
| *G01J 3/00* | (2006.01) | |
| *G02B 7/09* | (2006.01) | |
| *G01N 21/25* | (2006.01) | |
| *G02B 21/00* | (2006.01) | |
| *G02B 21/24* | (2006.01) | |
| *G01N 21/65* | (2006.01) | |

(52) U.S. Cl.
CPC ................ *G02B 7/09* (2013.01); *G01N 21/255* (2013.01); *G01N 21/65* (2013.01); *G02B 21/0032* (2013.01); *G02B 21/0052* (2013.01); *G02B 21/245* (2013.01); *G01N 2021/653* (2013.01)

(58) Field of Classification Search
CPC ............. G01N 2021/653; G01N 21/65; G02B 21/0032; G02B 21/0052; G02B 21/245
See application file for complete search history.

(56) References Cited

U.S. PATENT DOCUMENTS

| | | | | |
|---|---|---|---|---|
| 5,035,476 | A | * | 7/1991 | Ellis et al. ................... 359/202.1 |
| 5,084,612 | A | * | 1/1992 | Iwasaki et al. ................ 250/216 |
| 5,329,352 | A | * | 7/1994 | Jacobsen ....................... 356/301 |
| 5,808,746 | A | * | 9/1998 | Koishi et al. .................. 356/445 |

(Continued)

FOREIGN PATENT DOCUMENTS

| | | |
|---|---|---|
| CN | 1229927 A | 9/1999 |
| CN | 2416510 Y | 1/2001 |

(Continued)

OTHER PUBLICATIONS

T. Wilson, and C. Sheppard : Theory and Practice of Scanning Optical Microscopy : Academic Press, London (1984).

(Continued)

*Primary Examiner* — Kara E Geisel
*Assistant Examiner* — Rufus Phillips
(74) *Attorney, Agent, or Firm* — Mattingly & Malur, PC

(57) ABSTRACT

For an optical device as a transmission-type scanning optical microscope having a pinhole or a slit for limiting the amount of a detected light beam, a method of moving a scanning beam without moving an observation sample to be scanned is realized. A scanning beam from a beam scanning mechanism that has passed through an observation sample is focused onto a reflection plate, and is then returned back again to the observation sample. A light beam that has returned back from the sample is further fed back to the beam scanning mechanism, and then, the light beam that has been limited through a fixed pinhole or a slit is detected with a photodetector.

10 Claims, 10 Drawing Sheets

(56) References Cited

U.S. PATENT DOCUMENTS

| | | | |
|---|---|---|---|
| 6,169,289 B1 * | 1/2001 | White et al. | 250/458.1 |
| 7,352,472 B2 * | 4/2008 | Krijnen | 356/500 |
| 8,792,156 B1 * | 7/2014 | Kieu et al. | 359/327 |
| 2010/0188496 A1 * | 7/2010 | Xie et al. | 348/79 |

FOREIGN PATENT DOCUMENTS

| | | |
|---|---|---|
| CN | 102068236 A | 5/2011 |
| CN | 102116930 A | 7/2011 |
| CN | 202101940 U | 1/2012 |
| CN | 202204470 U | 4/2012 |
| JP | 3-188408 A | 8/1991 |
| JP | 4-27909 A | 1/1992 |
| JP | 2001-56438 A | 2/2001 |
| JP | 2009-230021 A | 10/2009 |

OTHER PUBLICATIONS

Chinese Office Action received in corresponding Chinese Application No. 201310352686.6 dated Jun. 12, 2015.
Masters Degree Thesis of Zhejiang University, Mar. 15, 2003.
Japanese Office Action received in corresponding Japanese Application No. 2012-188375 dated Dec. 15, 2015.

* cited by examiner

OPTICAL DEVICE FOR TRANSMISSION-TYPE SCANNING BY MOVING SCANNING BEAM WITHOUT MOVING OBSERVATION SAMPLE

CLAIM OF PRIORITY

The present application claims priority from Japanese patent application JP 2012-188375 filed on Aug. 29, 2012, the content of which is hereby incorporated by reference into this application.

BACKGROUND

1. Technical Field

The present invention relates to an optical device that requires an optical spatial resolution, and in particular, relates to an optical device that focuses a light beam onto an observation sample and relatively changes the light beam irradiation position with respect to the observation sample to acquire a response signal.

2. Background Art

A scanning optical microscope scans an observation sample (a sample to be observed) with a light beam by narrowing the light beam into a minute spot down to the diffraction limit. It is known that when a light beam from an observation sample is detected with a large area detector, the same resolution as that of a conventional microscope is attained. The conventional optical microscope as referred to herein irradiates a wide range of an area of an object with a light beam, and forms an image of the irradiated object through an objective lens. It is known that when a response beam of the beam, which has been focused onto the observation sample, is detected through a pinhole, the resolution will improve (Non-Patent Document 1). This is commercially available as a confocal scanning optical microscope.

There are known two scanning methods for the confocal scanning optical microscope. One is a method of directly moving an observation sample with respect to a focused spot. This method is advantageous in that the design of the optics is easy, optical aberrations generated in the optical spot are small, the scanning range is wide, and the like. However, this method is disadvantageous in that the scanning time is difficult to be reduced, a soft observation sample in a liquid could shake due to the scanning, and the like. The other scanning method is a method of fixing an observation sample and moving a scanning optical spot. This method can increase the scanning speed and can also handle a soft observation sample in a liquid. However, this method is disadvantageous in that the scanning optics are complex.

FIG. 11 shows optics of a reflection-type confocal scanning optical microscope. The scanning method used herein is a method of moving a scanning light beam. A laser beam emitted from a laser source 101 is collimated by lenses 261 and 208, and is reflected by a half mirror 262, and then enters a two-dimensional scanning mechanism 263 as an incident beam 302. The two-dimensional scanning mechanism includes two galvanometer mirrors, for example. The angle of the light beam output from the two-dimensional scanning mechanism 263 with the optical axis changes due to the scanning, and is obliquely output like an output light beam 300, for example. The light beam output from the two-dimensional scanning mechanism 263 is, after entering an objective lens 201, focused as a minute spot onto an observation sample 202. A laser beam 301 with such a minute light spot is reflected by the observation sample 202, and then returns back to the objective lens 201. The angle of the laser beam, which returns from the objective lens 201 to the two-dimensional scanning mechanism 263, with the optical axis is the same as that when the laser beam has entered the two-dimensional scanning mechanism 263. Therefore, the returning laser beam propagates along the same optical path as the incident light beam within the two-dimensional scanning mechanism, and becomes, when output from the two-dimensional scanning mechanism, a light beam that propagates along the same optical path as the fixed incident light beam 302. A reflected laser beam from the observation sample passes through the half mirror 262, and is focused onto a pinhole 265 by a condenser lens 264. Then, the transmitted beam is detected with a photodetector 104. The focused position of the laser beam on the pinhole 265 is not displaced regardless of the beam scanning. Thus, the detected intensity of the laser beam from the observation sample is not influenced by the scanning. Reference numeral 109 denotes an electronic device that captures a detection signal and controls the scanning position. The detection signal is displayed as an image on a display device 110.

FIG. 12 shows optics of a transmission-type confocal scanning optical microscope. In this case, a method of moving an observation sample to be scanned is adopted. A laser beam emitted from a laser source 101 is collimated by lenses 261 and 208 and is reflected by a half mirror 262. Then, the laser beam enters an objective lens 201 and is focused onto an observation sample 202. A laser beam that has passed through the observation sample 202 is focused onto a pinhole 265 by an objective lens 207 whose properties are close to the numerical aperture of the objective lens 201, and a condenser lens 205. A laser beam that has passed through the pinhole 265 is detected with a photodetector 104, and is captured by an electronic device 109. Scanning is performed by moving the observation sample 202. That is, the electronic device 109 moves and controls the position of a stage 200 that is integrated with the observation sample 202, using an actuator 102. When cells of a living organism and the like are observed as described above, a technology of slowly moving the stage 200, or fixing the cells on a holder fixed on the stage 200 should be used.

Non-Patent Document 1: T. Wilson, and C. Sheppard: Theory and Practice of Scanning Optical Microscopy: Academic Press, London (1984)

SUMMARY

When a transmission-type scanning optical microscope is used, it is often the case that an observation sample to be scanned is directly moved, but when an observation sample in a liquid is scanned, it would be impossible to increase the scanning speed. That is, if the scanning speed is increased, inconvenience would occur such that the observation sample shakes or moves, for example, which could result in a decrease in the optical resolution. Meanwhile, when cultured cells in the living state are observed, there may be cases where a stage for moving the observation sample is accompanied by a temperature control device or the like for keeping the cells alive. In such a case, the stage may preferably be not moved.

For example, when the transmission-type confocal optical microscope in FIG. 12 is used, if the observation sample 202 is fixed and is scanned with a light beam spot by the two-dimensional scanning mechanism, the focus position of the light beam on the pinhole 265 will be moved together with the scanning. Thus, the amount of a light beam detected through the pinhole will increase or decrease in synchronism with the scanning regardless of the tone of the observation sample, which is problematic.

It is an object of the present invention to, not only for a confocal optical microscope, but also for a transmission-type scanning optical microscope with detection optics having an aperture such as a pinhole or a slit arranged therein, realizing optics that can obtain a stable detection signal when an observation sample is fixed and is scanned with a light beam.

SUMMARY

An optical device in accordance with one aspect of the present invention includes a laser source; a beam scanning mechanism configured to move a scanning laser beam emitted from the laser source; a stage configured to hold an observation sample; an objective lens configured to focus the laser beam output from the beam scanning mechanism onto the observation sample held on the stage; condenser optics provided on a light-transmission side of the stage; a reflection plate arranged at a focal position of the condenser optics; a condenser lens configured to focus a light beam returning back from the beam scanning mechanism; an aperture arranged at a focal position of the condenser lens; a photodetector configured to detect a light beam that has passed through the aperture; a storage unit configured to store a signal of the photodetector in association with a scanning position; and a display device configured to display the signal stored in the storage unit.

An optical device in accordance with another aspect of the present invention includes a laser source; a beam scanning mechanism configured to move a scanning laser beam emitted from the laser source; a stage configured to hold an observation sample; a first objective lens configured to focus the laser beam output from the beam scanning mechanism onto the observation sample held on the stage; a second objective lens provided on a light-transmission side of the stage; a retroreflection plate configured to cause a laser beam that has passed through the second objective lens to return back to the second objective lens; a condenser lens configured to focus a light beam returning back from the beam scanning mechanism; an aperture arranged at a focal position of the condenser lens; a photodetector configured to detect a light beam that has passed through the aperture; a storage unit configured to store a signal of the photodetector in association with a scanning position; and a display device configured to display the signal stored in the storage unit.

The beam scanning mechanism can be configured as either a two-dimensional scanning mechanism or a three-dimensional scanning mechanism. The optical device may further include an actuator configured to move the position of a lens of the condenser optics or the position of the reflection plate in the optical-axis direction so that the position of the focus spot from the condenser optics always coincides with the position of the reflection plate, or an actuator configured to move the position of the second objective lens in the optical-axis direction so that a laser beam that has passed through the second objective lens enters the retroreflection plate as a collimated beam; a detector configured to capture a part of the returning light beam output from the scanning optics; and a feedback circuit configured to drive the actuator using a focus error signal.

According to the present invention, an observation sample can be fixed in a transmission-type scanning optical microscope. Thus, image data on a soft object (e.g., cells of a living organism) in a liquid can be acquired at a high speed. Accordingly, the time to acquire three-dimensional image data can be reduced.

Other problems, configurations, and advantages will become apparent from the following description of embodiments.

DETAILED DESCRIPTION

Hereinafter, embodiments for implementing the optical device of the present invention will be described with reference to the drawings.

Embodiment 1

Figure 1:
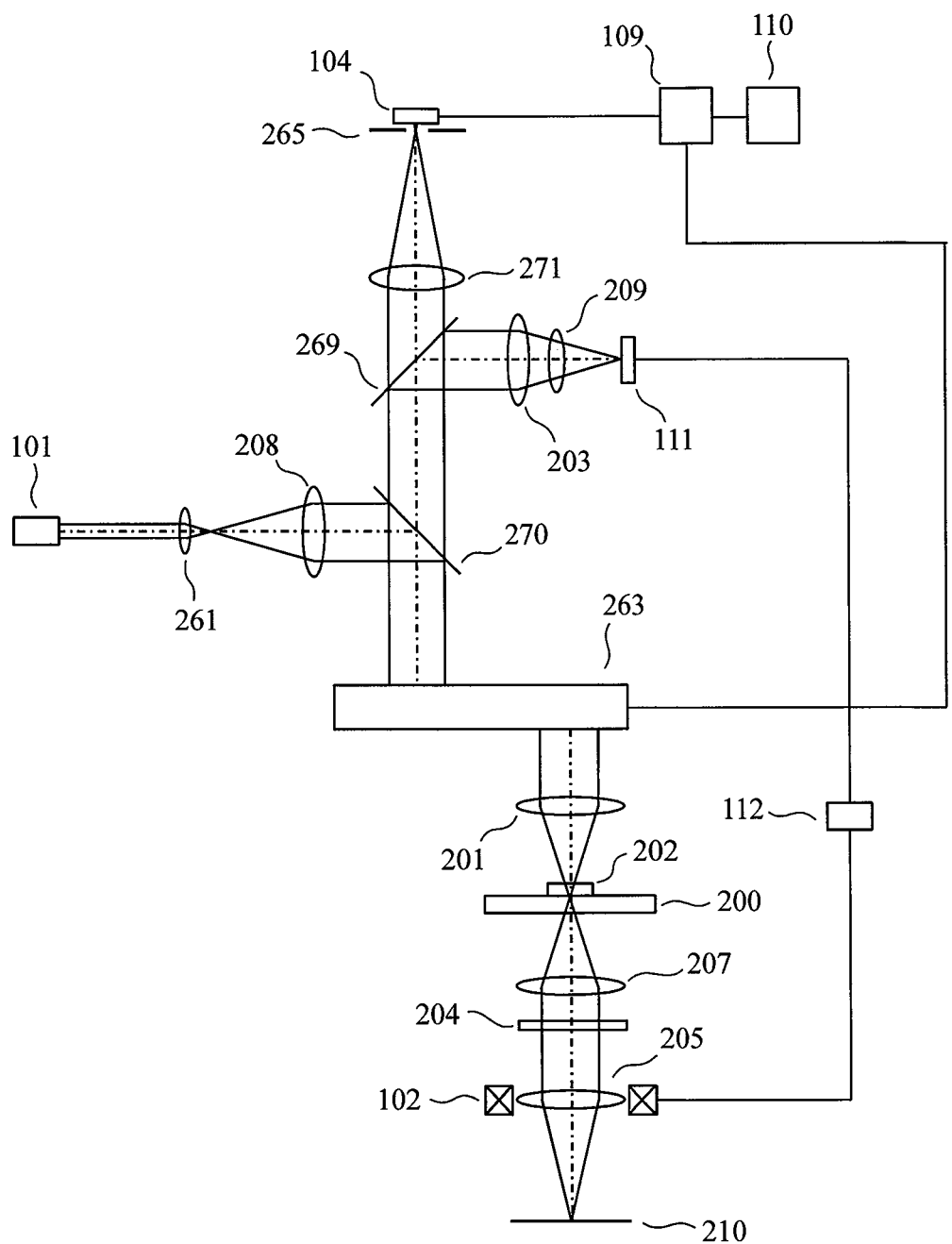
FIG. 1 is a schematic view showing an example of optics of an optical device in accordance with the present invention.

FIG. 1 is a schematic view showing an example of optics of an optical device in accordance with the present invention. This embodiment illustrates a transmission-type confocal scanning optical microscope that performs beam scanning.

For a laser source 101, either a pulsed laser or a continuous-wave laser can be used. A laser beam emitted from the laser source 101 is made an s-polarized light beam, and is collimated by lenses 261 and 208. The incident laser beam in the s-polarized state is reflected by a polarization beam splitter 270, and then enters a two-dimensional scanning mechanism 263. The two-dimensional scanning mechanism 263 includes two galvanometer mirrors, for example. A light beam whose angle with the optical axis has been changed by the two-dimensional scanning mechanism 263 enters an objective lens 201, and then irradiates an observation sample 202 at a minute spot. The observation sample 202 is arranged on a stage 200, but the stage 200 does not have a scanning function and is mainly used to position the observation sample 202. A laser beam that has passed through the observation sample 202 is focused onto a reflection plate 210 by objective lenses 207 and 205. The reflection plate 210 in this embodiment is a plane mirror. A λ/4 plate 204 is arranged between the objective lenses 207 and 205, which circularly polarizes the light beam onto the reflection plate 210.

The beam reflected by the reflection plate 210 is inverted in the circularly polarized state, and then returns to the lens 205 and passes through the λ/4 plate 204 again. The polarized state of the laser beam at this time becomes the p-polarized beam. The numerical aperture of the objective lens 207 is about equal to that of the objective lens 201, and the laser beam is focused again onto the observation sample 202. The spot position is the same as the position where the laser beam has been initially focused onto the observation sample by the objective lens. Such a relationship is maintained even when the beam scanning position has changed. Thus, the optical path of the returning laser beam, inclusive of its angle made with the optical axis, is the same as that of the light beam incident on the observation sample. Thus, the optical axis of the laser beam that returns to the polarization beam splitter 270 from the two-dimensional scanning mechanism 263 is fixed independently of the scanning. As the laser beam is the p-polarized beam, it passes through the polarization beam splitter 270, and is partially reflected by the half mirror 269. Such reflected beam is used to control the reflection plate 210 so that it is always in the focal position.

Figure 2:
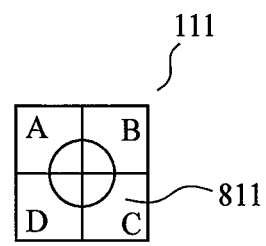
FIG. 2 is a schematic view showing a four-split detector for detecting defocus.

A focal position control method adopted in this embodiment is the astigmatic method. Reference numeral 203 denotes a condenser lens, and reference numeral 209 denotes a cylindrical lens. A photodetector 111 is arranged at the position of the least circle of confusion. FIG. 2 is a schematic view showing the sensitive regions of the photodetector 111. The photodetector 111 has four split sensitive regions, and an irradiation laser beam irradiates the photodetector in the state of the least circle of confusion 811. Electric signals from the respective detectors are represented by A, B, C, and D. Using such signals, the electronic circuit 112 generates a focal position control signal AF. The control signal AF is represented as: AF=(A+C)−(B+D). The control signal AF is provided to an actuator 102 as a feedback signal, so that focus is achieved on the reflection plate 210. Although focus control is performed using the astigmatic method in this embodiment, other focus control methods such as the knife-edge method may also be used.

A laser beam that has passed through the half mirror 269, that is, a beam returning back from the two-dimensional scanning mechanism 263 is focused onto a pinhole 265 by a lens 271, and is detected with a photodetector 104. The detected signal is processed by an electronic device 109. The scanning position of the two-dimensional scanning mechanism is controlled by the electron device 109, and a detection signal from the photodetector 104 is stored in the electronic device 109 in association with the scanning position. The stored signal is displayed as an image on the image display device 110.

Although this embodiment uses a polarization beam splitter or the like to improve the light use efficiency, the object of the present invention can also be achieved even when a half beam splitter is used.

Embodiment 2

Figure 3:
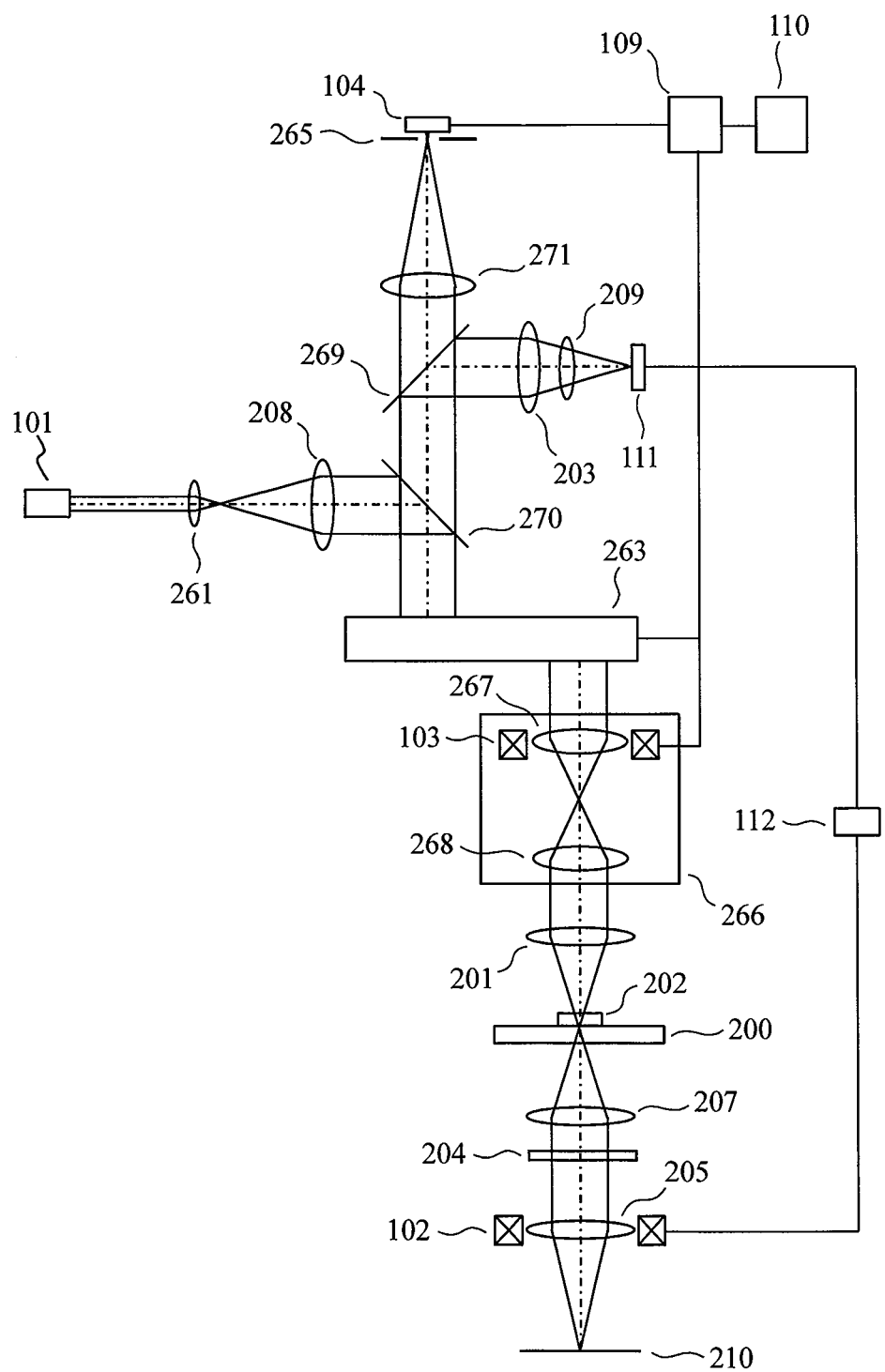
FIG. 3 is a schematic view showing an example of optics of an optical device capable of three-dimensional scanning in accordance with the present invention.

FIG. 3 shows an example of a second optical device that is based on the present invention. In the optical device in this embodiment, a z-direction scanning mechanism 266 is added to the optical device in Embodiment 1.

A laser beam output from the two-dimensional scanning mechanism 263 enters the z-direction scanning mechanism 266. The z-direction scanning mechanism 266 includes two lenses 267 and 268 and an actuator 103. The actuator 103, which operates upon receiving an instruction from the electronic device 109, realizes the beam spot scanning in the z-direction by changing the position of the lens 267 in the optical axis direction, that is, in the z-axis direction. When a gap between the lenses is changed, the divergence angle of the light beam incident on the objective lens 201 will change, and the position of the minimum spot of the beam output from the objective lens 201 will also change in the z direction correspondingly. Such defocus is sensed by the photo detector 111, and a feedback signal is generated by the electronic circuit 112 and is provided to the actuator 102. Accordingly, the actuator 102 moves the lens 205 to the focal position, so that focus errors on the reflection plate 210 are modified to be smaller. Accordingly, even if the beam scanning is performed in the three-dimensional direction, the detection signal will not be disturbed by the scanning as the position of the laser beam from the observation sample on the pinhole 265, inclusive of the optical axis direction thereof, is always fixed on the pinhole.

Embodiment 3

Figure 4:
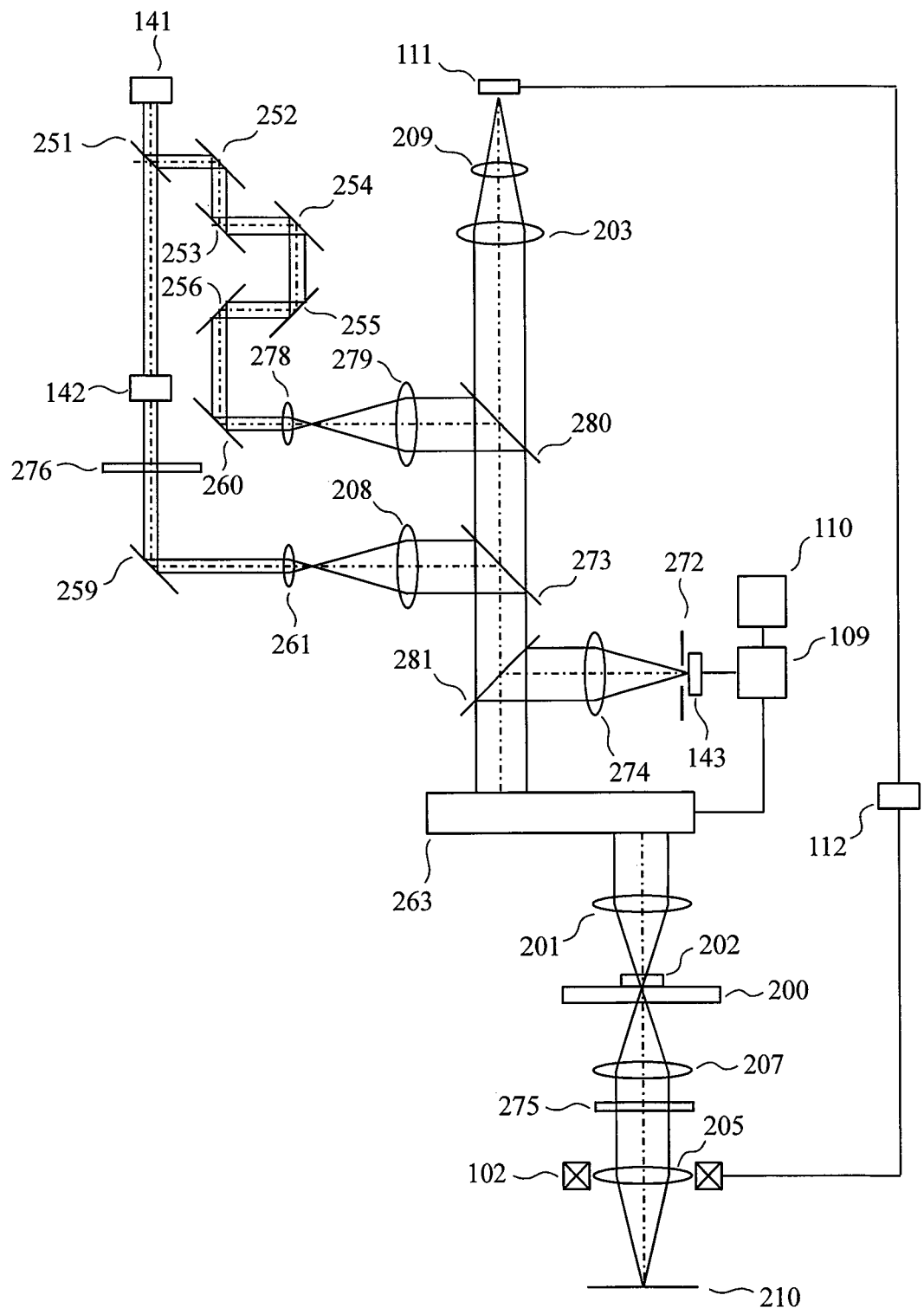
FIG. 4 is a schematic view showing an example of optics of an optical device that detects CARS in accordance with the present invention.

FIG. 4 shows an embodiment in which the present invention is applied to a multiplex CARS scanning microscope. The details of the multiplex CARS scanning microscope are described in, for example, M. Okuno, and et al, Opt. Lett., Vol. 33, PP. 923-925 (2008).

CARS is the acronym of Coherent Anti-Stokes Raman Scattering. When a measurement method that detects a CARS beam is used, it is possible to non-invasively observe cells of a living organism and also obtain information on molecules in the vibrational state. Thus, estimation of the types of biological matters is possible. It is often the case that a CARS beam is generated strongly in the transmission direction from a biological sample. Thus, the CARS beam is detected on the transmission side. In addition, a multiplex CARS scanning microscope requires a spectrometer with a slit. From such circumstances, a transmission-type multiplex CARS scanning microscope adopts a method of moving an observation sample to be scanned in order not to cause the CARS beam to deviate from the slit due to the scanning.

In this embodiment, an observation sample to be scanned is not moved, but a scanning beam is moved.

Figure 5:
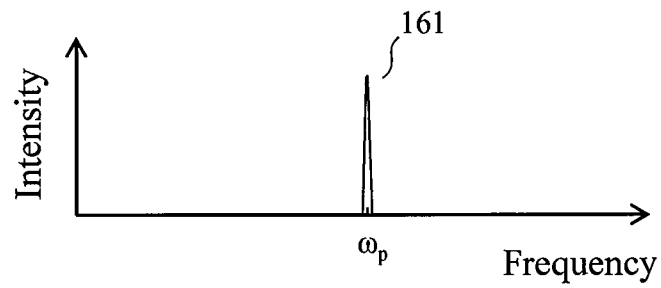
FIG. 5 is a diagram showing the frequency spectrum of a pulsed laser beam.
Figure 6:
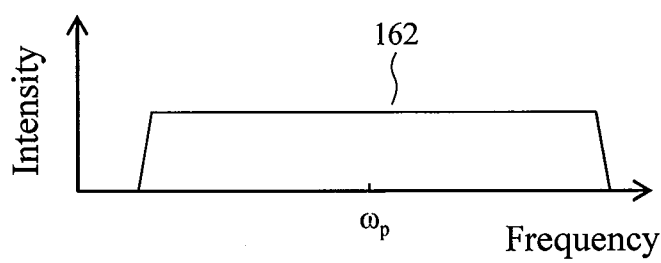
FIG. 6 is a diagram showing the frequency spectrum of a supercontinuum beam.
Figure 7:
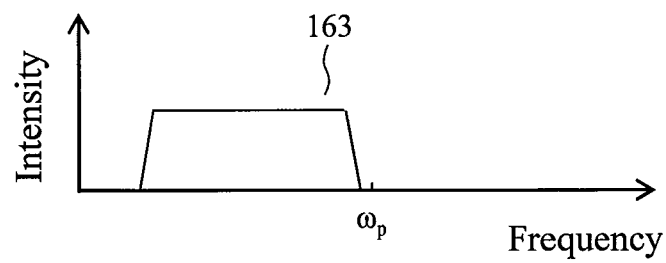
FIG. 7 is a diagram showing the frequency spectrum of a supercontinuum beam in the low-frequency region used as a Stokes beam.

A pulsed laser source 141 emits a laser beam 161 with the center frequency $\omega_P$ shown by a spectrum in FIG. 5. The emitted laser beam is a p-polarized beam and is split into two beams by a beam splitter 251. Thus, a beam that has passed through the beam splitter 251 enters a polarization-preserving photonic crystal fiber 142. The incident light beam is converted into a light beam such as the one shown by a spectrum 162 in FIG. 6, which is called a SC beam (a supercontinuum beam). Although a SC beam is obtained using a photonic crystal fiber herein, the SC beam can also be obtained using other means such as a dispersion-flattened/dispersion-decreasing fiber or a bidirectional tapered fiber. The SC beam has a wide wavelength range including the excitation light frequency $\omega_P$, and its coherent property is retained. With regard to the SC beam, the low-pass filter 276 transmits only a beam with a lower frequency than the frequency $\omega_P$. That is, the low-pass filter transmits a beam in the low-frequency region 163 shown in FIG. 7. The beam that has passed through the low-pass filter 276 is reflected by a mirror 259, and is used as a Stokes beam with a broadband frequency $\omega_{ST}$. The Stokes beam is collimated by lenses 261 and 208, and is then reflected by a dichroic mirror 273 that reflects the wavelength region of the Stokes beam.

Meanwhile, a laser beam with the center frequency $\omega_P$ to be used as a pump beam, which has been reflected by the beam splitter 251, is further reflected by a mirror 252 and a group of mirrors 253, 254, 255, 256, and 260 for adjusting the optical path difference. Then, the laser beam is collimated by lenses 278 and 279. The pump beam is then reflected by a half mirror 280, and enters the dichroic mirror 273, and the two beams (the pump beam and the Stokes beam) become coaxial beams. The coaxial beams pass through a dichroic mirror 281 (which transmits the pump beam and the Stokes beam), and enter a two-dimensional scanning mechanism 263.

The pump beam and the Stokes beam are focused onto an observation sample 202 on a stage 200 by an objective lens 201. A CARS beam with a frequency of $\omega_{AS}=2\omega_P-\omega_{ST}$ generated from the observation sample propagates in the same transmission direction as the pump beam and the Stokes beam, and is focused onto a reflection plate 210 by objective lenses 207 and 205. A dichroic filter 275 with a high-pass filter function is arranged between the objective lenses 207 and 205, and removes a CARS beam that is initially generated from the observation sample when it transmits the pump beam and the Stokes beam.

The pump beam and the Stokes beam reflected by the reflection plate 210 return along the same optical path, and cause a CARS beam to be generated from the observation sample 202 again. The pump beam, the Stokes beam, and the CARS beam return to the two-dimensional scanning mechanism 263, and only the CARS beam is reflected by the dichroic mirror 281. The CARS beam is focused onto a slit 272 of a spectrometer 143 by a lens 274. The data from the spectrometer is processed by an electronic device 109, and is displayed by a display device 110. The electronic device 109 removes the non-resonant components of the CARS beam using the maximum entropy method. Among the light beams other than the CARS beam that have passed through the dichroic mirror 281, only the pump beam passes through the next dichroic mirror 273. The pump beam passes through the half mirror 280, and is focused onto a photodetector 111 with four split sensitive regions by a lens 203 and a cylindrical lens 209, and is then detected at the position of the least circle of confusion. This signal is processed by an electronic circuit 112, and controls an actuator 102 as a focus error signal.

The dichroic filter 275 removes the initially generated CARS beam. However, the dichroic filter 275 can be removed if no problem occurs on the spectrum data when the CARS beam irradiates the observation sample.

Embodiment 4

This embodiment is an embodiment for implementing the homodyne detection method using the phase diversity method for the multiplex CARS scanning optical microscope shown in Embodiment 3.

Figure 8:
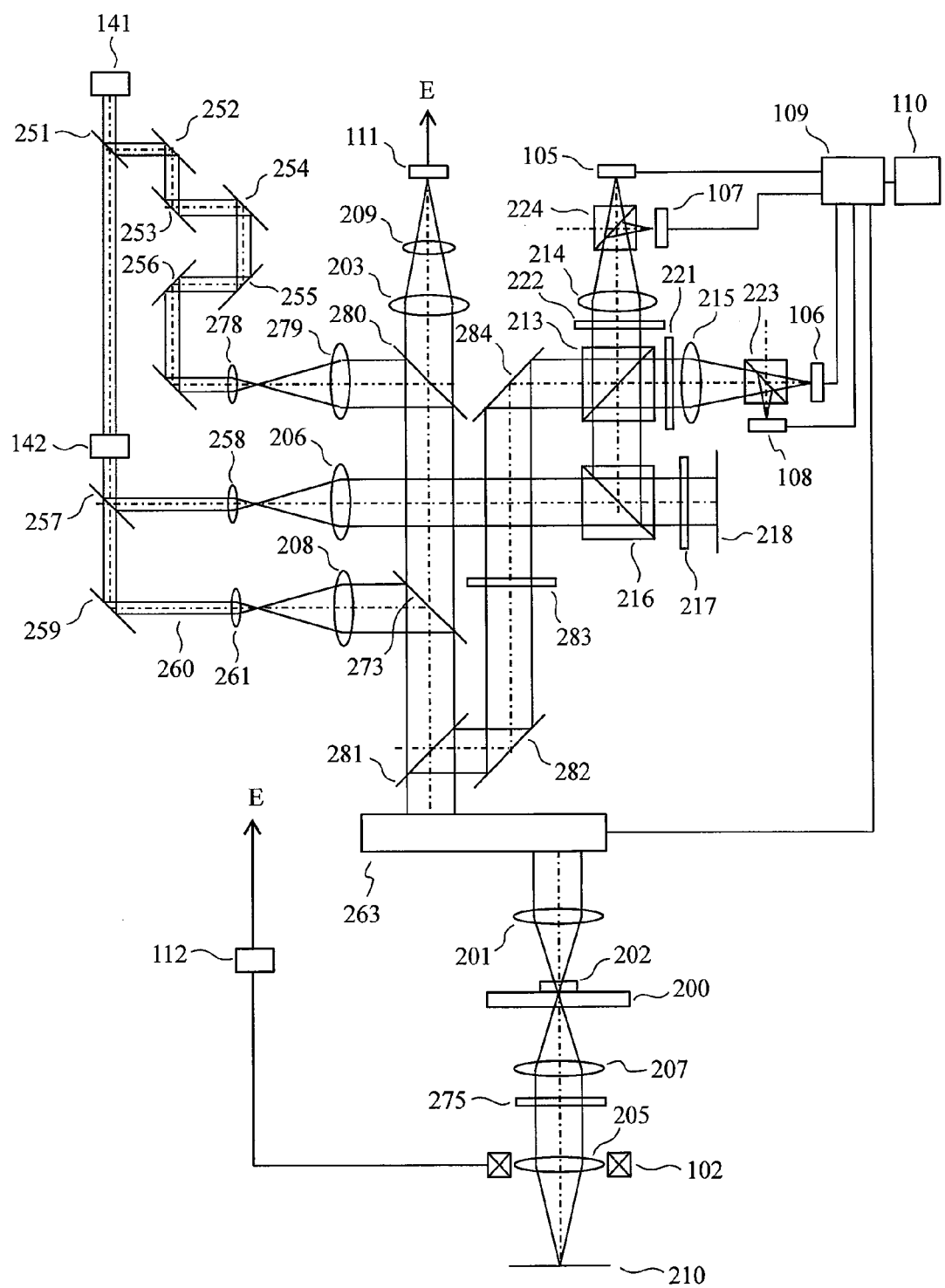
FIG. 8 is a schematic view showing an example of optics of an optical device that detects CARS in accordance with the present invention.
Figure 9:
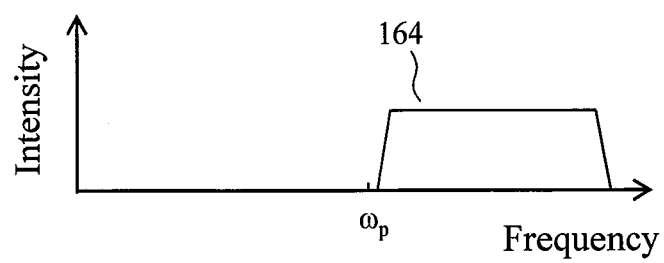
FIG. 9 is a diagram showing the frequency spectrum of a supercontinuum beam in the high-frequency region used as a reference beam.

FIG. 8 is a schematic view of an optical device in this embodiment. A pulsed laser source 141 and a photonic crystal fiber 142 have similar properties to those in Embodiment 3. A p-polarized SC beam from the photonic crystal fiber 142 is split into two beams by a dichroic mirror 257. The reflected beam is a SC beam with a spectrum shape 164 in FIG. 9, and the transmitted beam has a spectrum 163 shown in FIG. 7. The spectrum 164 is a wavelength region of the anti-Stokes beam, and is used as a reference beam for homodyne detection.

The SC beam in the wavelength region that has passed through the dichroic mirror 257 is, after being reflected by a mirror 259, collimated by lenses 261 and 208, and is then reflected by a dichroic mirror 273. This SC beam is used as a Stokes beam to generate CARS. A pump beam to generate CARS is reflected by a half mirror 280, and becomes a p-polarized beam that is coaxial with the Stokes beam, and then enters a two-dimensional scanning mechanism 263. A beam output from the two-dimensional scanning mechanism 263 is focused onto an observation sample 202 by an objective lens 201, and the transmitted beam is further focused onto a reflection plate 210 by lenses 207 and 205. A reflected beam that has returned from the reflection plate 210 to the group of lenses irradiates the observation sample 202 again, and causes a CARS beam to be generated mainly in the transmission direction. Among the pump beam, the Stokes beam, and the CARS beam that have returned to the objective lens 201 and the two-dimensional scanning mechanism 263, the CARS beam is reflected by a dichroic mirror 281 and a mirror 282, and then, only p-polarized components thereof pass through an analyzer 283. The p-polarized CARS beam is reflected by a mirror 284 and then enters a half beam splitter 213.

The p-polarized SC beam in the high-frequency region (reference beam) is collimated by lenses 258 and 206, and passes through a polarization beam splitter 216 and a Fresnel rhomb wave plate 217 having the effect of a λ/4 plate, and is then returned back to the Fresnel rhomb wave plate 217 by a mirror 218. The mirror 218 is used to adjust the optical path length. A laser beam that has passed through the Fresnel rhomb wave plate 217 is an s-polarized beam, and is reflected by the polarization beam splitter 216 to be directed toward the beam splitter 213.

It follows that light beams polarized in different directions enter the half beam splitter 213 from two directions, and the light beams are split in two directions, so that interference light beams are output in two directions. In order to detect the absolute value of the electric field of the CARS beam, interference measurement is performed using a known method called phase diversity detection. Symbol $\omega$ denotes the spectrum frequency. A Fresnel rhomb wave plate 221 having the effect of a λ/2 plate by which the optical axis is tilted by 22.5° is arranged for interference light beams that emerge to the right of the half beam splitter on the paper surface. Thus, the interference light beams are focused onto slits of spectrometers arranged at the focal positions by a condenser lens 215. A polarization beam splitter 223 is arranged on the optical path at a position before the beam splitters, and decomposes the interference light beams into s-direction components and p-direction components, so that the respective components are detected with a spectrometer 106 and a spectrometer 108.

Herein, suppose that the observation sample is a point object on the optical axis of the focal plane, and the complex amplitude of the CARS beam from the observation sample and that of the reference beam are $E_{AS}(\omega)$ and $E_{LO}$, respectively. Then, provided that the difference signal between the beam splitters 106 and 108 at their respective wavelengths is $I_C(\omega)$, $$I_C(\omega)=\alpha|E_{AS}(\omega)|\cdot|E_{LO}|\cos\Phi(\omega),$$

where $\alpha$ represents a coefficient including the signal amplification, beam splitter efficiency, and the like, and $\Phi(\omega)$ represents the phase difference between the CARS beam from the observation sample and the reference beam.

In addition, a Fresnel rhomb wave plate 222 having the effect of a λ/4 plate by which the optical axis is tilted by 45 degrees is inserted into the interference light beams that emerge in the upward direction of the half beam splitter 213 on the paper surface. The interference light beams focused by the condenser lens 214 are detected through slits of spectrometers 105 and 107. After the interference light beams are separated into an s-polarized beam and a p-polarized beam by a polarization beam splitter 224 arranged on the optical path, the beams are detected by the respective spectrometers.

Herein, provided that the difference signal between the spectrometers 105 and 107 at their respective wavelengths is $I_S(\omega)$, $$I_S(\omega)=\alpha|E_{AS}(\omega)|\cdot|E_{LO}|\sin \Phi(\omega).$$

For $I_C(\omega)$ and $I_S(\omega)$, only the interference components are detected. The electronic device 109 performs computation of the phase difference $\Phi(\omega)$ at the same time as performing the computation of:

$$I(\omega)=\sqrt{(I_C^2+I_S^2)}=\alpha|E_{AS}(\omega)|\cdot|E_{LO}| \quad (1)$$

$I(\omega)$ is proportional to the amplitude of the CARS beam from the observation sample and the amplitude of the reference beam. Therefore, increasing $|E_{LO}|$ having no wavelength dependence can obtain $I(\omega)$ in the form with the amplified $|E_{AS}(\omega)|$. Typically, the spectrum of a SC beam is not flat. Therefore, in order to obtain a more accurate spectrum $I(\omega)$, correction should be performed using the amplitude spectrum of the SC beam.

Next, a phase difference $\theta_S(\omega)$ generated in the resonance term is determined using a reference sample that generates a CARS beam with only non-resonance components. Accordingly, the complex components $[I(\omega)\sin \theta_S(\omega)]$ of the resonance term are extracted. A raw CARS spectrum that has not been processed is influenced by the non-resonance term and has a different shape from a typical Raman spectrum. Thus, the finding of the Raman spectrum accumulated heretofore cannot be used. However, as $[I(\omega)\sin \theta_S(\omega)]$ is about the same as the Raman spectrum, the conventional finding of the Raman spectrum can be used.

For a detector in the spectrometer, a CCD or the like is used. Reference numeral 110 denotes a display device that displays the scanning position and the display position of the observation sample 202 in association with each other. By displaying the intensity distribution of $[I(\omega)\sin \theta_S(\omega)]$ at the frequency position $\omega$ that is characteristic to the molecular vibration of a particular molecule, the distribution of the molecule can be known.

Among the light beams that have returned to the two-dimensional scanning mechanism 263, those other than the CARS beam pass through the dichroic mirror 281, and only the pump beam passes through the dichroic mirror 273. The pump beam passes through the half mirror 280, and is focused onto a four-split photodetector 111 by a lens 203 and a cylindrical lens 209. The detected signal is processed by an electronic circuit 112, and is fed back to an actuator 102 as a focus error signal. Accordingly, the reflection plate 210 is maintained at the focal position.

In this embodiment, the actuator 102 is configured to drive the lens 205, but may also be configured to drive the reflection plate 210 or the objective lens 207. In particular, as the weight of the reflection plate 210 can be reduced, the size of the actuator used can be small.

Embodiment 5

Figure 10:
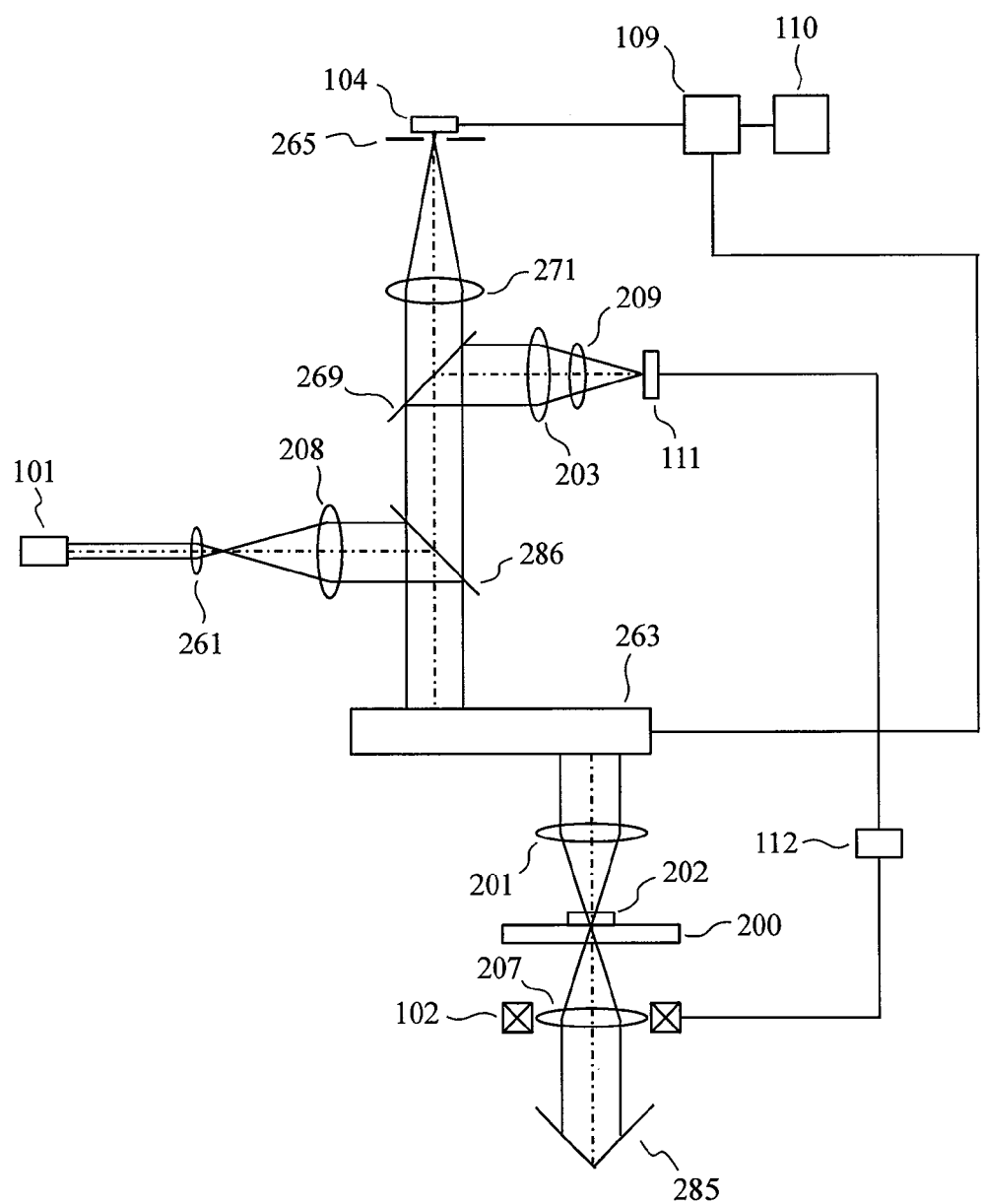
FIG. 10 is a schematic view showing an example of optics of an optical device in accordance with the present invention.
Figure 11:
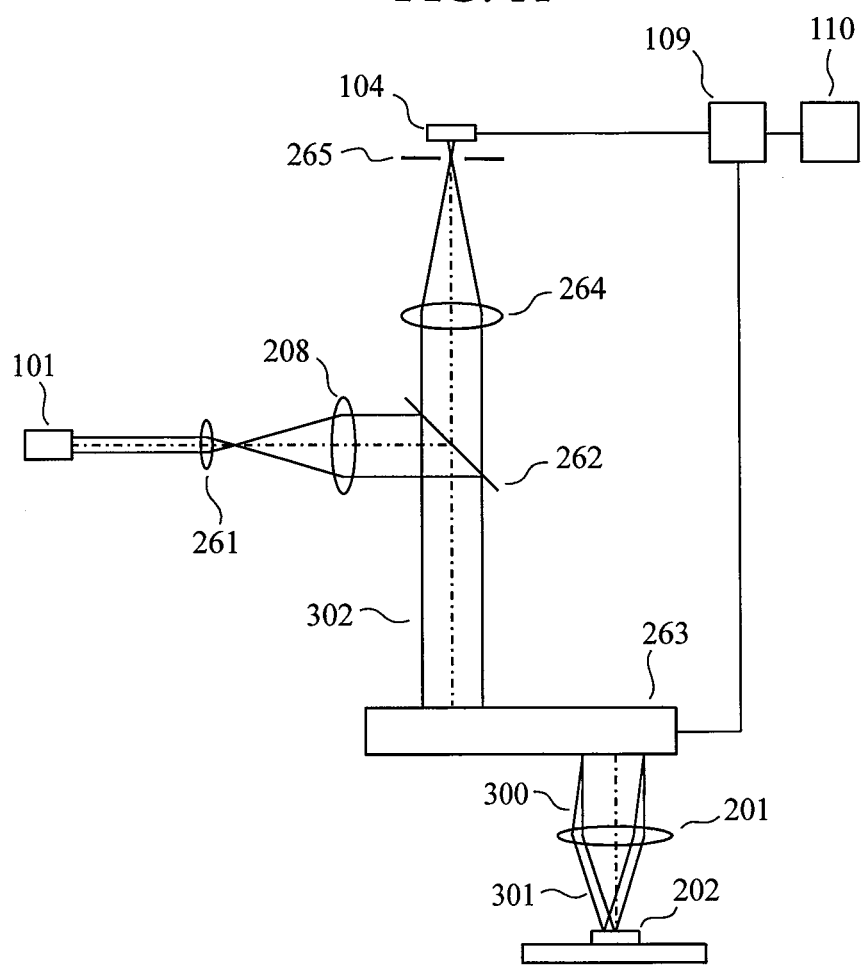
FIG. 11 is a view showing optics of a reflection-type confocal optical microscope.
Figure 12:
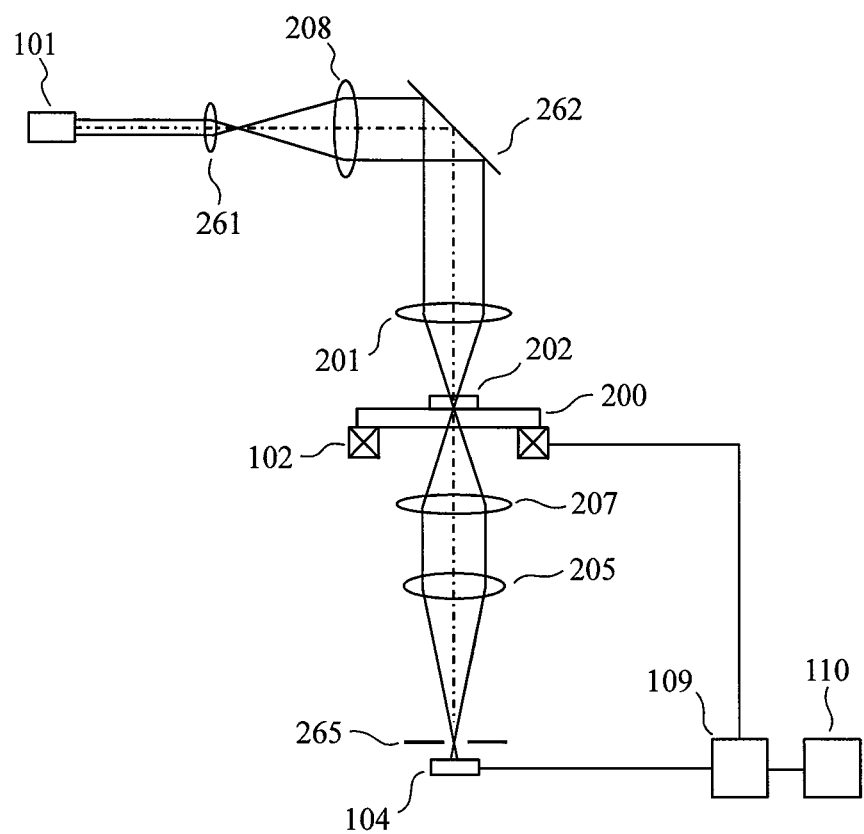
FIG. 12 is a diagram showing optics of a transmission-type confocal optical microscope.

FIG. 10 is a schematic view showing another embodiment of an optical device in accordance with the present invention. Herein, a transmission-type confocal scanning optical microscope that moves a scanning beam as in Embodiment 1 is realized.

The optical difference from Embodiment 1 is in that an ordinary beam splitter 286 is used instead of the polarization beam splitter 270 used in Embodiment 1, and also in the optics for processing a laser beam that has passed through the observation sample 202.

A laser beam that has passed through the observation sample 202 is collimated by an objective lens 207, and is directed toward a corner cube 285 as a retroreflection plate. As a corner cube has a property of causing an incident light beam to return in the same direction as the incident direction, it is possible to focus the laser beam reflected by the corner cube at the same scanning position again through the objective lens 207 even when the irradiation position on the observation sample 202 has been changed by the two-dimensional scanning mechanism 263. Accordingly, a laser beam from the observation sample is still on the pinhole 265 as in Embodiment 1, and the influence of the laser scanning does not reach the detection signal. It should be noted that the objective lens 207 can be driven in the optical axis direction by the actuator, and is controlled to always cause parallel beams to enter the corner cube.

Although an example in which a corner cube is used as the retroreflection plate is shown herein, it is also possible to use other members as long as they have a property of causing the incident light beam to be reflected back in the incident direction again regardless of the incident angle.

It should be noted that the present invention is not limited to the aforementioned embodiments, and includes various variations. For example, although the aforementioned embodiments have been described in detail to clearly illustrate the present invention, the present invention need not include all of the structures described in the embodiments. It is possible to replace a part of a structure of an embodiment with a structure of another embodiment. In addition, it is also possible to add, to a structure of an embodiment, a structure of another embodiment. Further, it is also possible to, for a part of a structure of each embodiment, add/remove/substitute another structure. For example, the reflection plate 210 in Embodiments 2 to 4 can be replaced with the retroreflection plate 285 illustrated in Embodiment 5, and the objective lenses 207 and 205 can be replaced with the objective lens 207 such as the one illustrated in Embodiment 5.

The present invention can be applied to a transmission-type scanning optical microscope having an aperture, such as a pinhole or a slit for limiting a detection light beam, arranged at a position before a detector that detects a signal. Examples of such microscope include a transmission-type confocal microscope and a multiplex CARS scanning microscope.

REFERENCE SIGNS LIST

101: Laser source
102, 103 102, 103: Actuators
104: Photodetector
105, 106, 107, 108: Beam splitters
109: Electronic device
110: Display device
111: Photodetector
112: Electronic circuit
141: Pulsed laser source
142: Photonic crystal fiber
143: Spectrometer
201: Objective lens
202: Observation sample
203: Condenser lens
205: Lens
207: Objective lens
209: Cylindrical lens
210: Reflection plate
213: Beam splitter
214: Condenser lens
216: Polarization beam splitter 217: Fresnel rhomb wave plate
218: Mirror
221: Fresnel rhomb wave plate
222: Fresnel rhomb wave plate
223: Polarization beam splitter
224: Polarization beam splitter
263: Two-dimensional scanning mechanism
265: Pinhole
266: z-direction scanning mechanism
272: Slit

What is claimed is:

1. An optical device comprising:
    a laser source;
    a beam scanning mechanism configured to move a scanning laser beam emitted from the laser source;
    a stage configured to hold an observation sample;
    an objective lens configured to focus the laser beam output from the beam scanning mechanism onto the observation sample held on the stage;
    condenser optics provided on a light-transmission side of the stage;
    a reflection plate;
    a condenser lens configured to focus a light beam returning back from the beam scanning mechanism;
    an aperture arranged at a focal position of the condenser lens;
    a photodetector configured to detect a light beam that has passed through the aperture;
    an electronic device configured to store a signal of the photodetector in association with a scanning position; and
    a display device configured to display the signal stored in the electronic device;
    optics configured to detect a part of the light beam returning back from the beam scanning mechanism to detect a focus error;
    an actuator configured to drive a lens of the condenser optics or the reflection plate in an optical-axis direction using a signal of the detected focus error
    another scanning mechanism including another actuator configured to move another lens arranged between the objective lens and the laser source in the optical-axis direction,
    wherein the electronic device generates instructions based on the detected focus error and sends the instructions to the actuator and to the another actuator to position the reflection plate at a focal position of the condenser optics.

2. The optical device according to claim 1, wherein the aperture is one of a pinhole or a slit.

3. The optical device according to claim 1, wherein the beam scanning mechanism is a two-dimensional scanning mechanism.

4. The optical device according to claim 1, wherein the beam scanning mechanism is a three-dimensional scanning mechanism.

5. The optical device according to claim 1, wherein a slit is used as the aperture, and a spectrometer is used as the photodetector.

6. The optical device according to claim 5, wherein the light beam returning back from the beam scanning mechanism includes a light beam with a different wavelength from a wavelength of an incident light beam.

7. The optical device according to claim 6, further comprising:
    an optical element configured to generate a supercontinuum beam using the laser beam emitted from the laser source as a pump beam; and
    optics configured to detect a part of the light beam returning back from the beam scanning mechanism to detect a focus error;
    wherein the observation sample is irradiated with the pump beam and a Stokes beam that is a part of the supercontinuum beam,
    wherein an anti-Stokes beam from the observation sample is analysed spectroscopically, and
    wherein the optics configured to detect a focus error obtain a focus error signal from the pump beam or the Stokes beam contained in the light beam returning back from the beam scanning mechanism.

8. The optical device according to claim 7, wherein a part of the supercontinuum beam has a frequency spectrum in a high-frequency region for use as a reference beam.

9. The optical device according to claim 6, further comprising:
    an optical element configured to generate a supercontinuum beam using the laser beam emitted from the laser source as a pump beam; and
    a photonic crystal fiber configured to detect a part of the light beam returning back from the beam scanning mechanism to detect a focus error;
    wherein the observation sample is irradiated with the pump beam and a Stokes beam that is a part of the supercontinuum beam,
    wherein an anti-Stokes beam from the observation sample is analyzed spectroscopically, and
    wherein the optics configured to detect a focus error obtain a focus error signal from the pump beam or the Stokes beam contained in the light beam returning back from the beam scanning mechanism.

10. The optical device according to claim 9, wherein the photonic crystal fiber is a polarization-preserving photonic crystal fiber.

* * * * *